United States Patent
Myllyoja et al.

(10) Patent No.: US 9,533,291 B2
(45) Date of Patent: *Jan. 3, 2017

(54) METHOD FOR PRODUCTION OF HYDROCARBONS BY INCREASING HYDROCARBON CHAIN LENGTH

(71) Applicant: Neste Oil Oyj, Espoo (FI)

(72) Inventors: Jukka Myllyoja, Vantaa (FI); Pekka Aalto, Porvoo (FI); Rami Piilola, Helsinki (FI)

(73) Assignee: Neste Oyj, Espoo (FI)

( * ) Notice: Subject to any disclaimer, the term of this patent is extended or adjusted under 35 U.S.C. 154(b) by 184 days.

This patent is subject to a terminal disclaimer.

(21) Appl. No.: 14/375,733

(22) PCT Filed: Nov. 1, 2012

(86) PCT No.: PCT/FI2012/051067
§ 371 (c)(1),
(2) Date: Jul. 30, 2014

(87) PCT Pub. No.: WO2013/113977
PCT Pub. Date: Aug. 8, 2013

(65) Prior Publication Data
US 2015/0018588 A1 Jan. 15, 2015

Related U.S. Application Data

(60) Provisional application No. 61/592,842, filed on Jan. 31, 2012.

(51) Int. Cl.
| | |
|---|---|
| C07C 5/27 | (2006.01) |
| C07C 1/20 | (2006.01) |
| C07C 1/24 | (2006.01) |
| C10G 3/00 | (2006.01) |
| B01J 27/051 | (2006.01) |
| C11C 3/12 | (2006.01) |
| C10L 1/04 | (2006.01) |
| B01J 35/00 | (2006.01) |
| B01J 23/04 | (2006.01) |
| B01J 23/883 | (2006.01) |
| C11C 1/00 | (2006.01) |
| C07C 45/54 | (2006.01) |
| C10M 105/24 | (2006.01) |
| B01D 3/00 | (2006.01) |
| B01J 23/887 | (2006.01) |
| C07C 1/22 | (2006.01) |
| C07C 45/41 | (2006.01) |
| C10M 105/04 | (2006.01) |
| C10M 177/00 | (2006.01) |
| B01J 37/20 | (2006.01) |
| B01J 21/06 | (2006.01) |

(52) U.S. Cl.
CPC .......... *B01J 27/0515* (2013.01); *B01D 3/009* (2013.01); *B01J 23/04* (2013.01); *B01J 23/883* (2013.01); *B01J 23/8872* (2013.01); *B01J 35/0006* (2013.01); *C07C 1/22* (2013.01); *C07C 1/24* (2013.01); *C07C 5/2735* (2013.01); *C07C 5/2737* (2013.01); *C07C 45/41* (2013.01); *C07C 45/54* (2013.01); *C10G 3/42* (2013.01); *C10G 3/44* (2013.01); *C10G 3/45* (2013.01); *C10G 3/46* (2013.01); *C10L 1/04* (2013.01); *C10M 105/04* (2013.01); *C10M 105/24* (2013.01); *C10M 177/00* (2013.01); *C11C 1/005* (2013.01); *C11C 3/123* (2013.01); *B01J 21/063* (2013.01); *B01J 37/20* (2013.01); *C07C 2523/16* (2013.01); *C07C 2523/42* (2013.01); *C07C 2523/44* (2013.01); *C07C 2523/46* (2013.01); *C07C 2523/745* (2013.01); *C07C 2523/75* (2013.01); *C07C 2523/755* (2013.01); *C10L 2200/0484* (2013.01); *Y02P 30/20* (2015.11)

(58) Field of Classification Search
None
See application file for complete search history.

(56) References Cited

U.S. PATENT DOCUMENTS

| | | | | |
|---|---|---|---|---|
| 7,967,973 | B2 * | 6/2011 | Myllyoja | ........... C11B 13/00 208/18 |
| 8,394,258 | B2 * | 3/2013 | Koivusalmi | ........... C11B 13/00 208/15 |
| 2007/0161832 | A1 | 7/2007 | Myllyoja et al. | |

FOREIGN PATENT DOCUMENTS

WO 2007068799 A2 6/2007

OTHER PUBLICATIONS

International Search Report PCT/FI2012/051067 dated Feb. 5, 2013.
Berenblyum et al: "On the mechanism of catalytic conversion of fatty acids into hydocarbons in the presence of palladium catalysts on alumina", Petroleum Chemistry, Sep. 30, 2011, 51-5, 336-341.
James et al: "A review on conversion of triglycerides to on-specification diesel fuels without additional inputs", International Journal of Energy Research, May 2012, 36-6, 691-702.

\* cited by examiner

*Primary Examiner* — Bobby Ramdhanie
*Assistant Examiner* — Philip Louie
(74) *Attorney, Agent, or Firm* — Andrus Intellectual Property Law, LLP

(57) ABSTRACT

The present invention provides a method for increasing hydrocarbon chain length. The method comprises providing a feedstock comprising fatty acids and/or fatty acid esters with hydrocarbon chain length below C23 into a reaction zone in which ketonization is conducted in the presence of a hydrotreatment catalyst under hydrogen pressure. The obtained ketones have a hydrocarbon chain length of from C24 to C43. The present invention further provides a method for simultaneous production of base oil components and fuel components.

13 Claims, No Drawings

METHOD FOR PRODUCTION OF HYDROCARBONS BY INCREASING HYDROCARBON CHAIN LENGTH

CROSS REFERENCE TO RELATED APPLICATION

The present application is the U.S. national stage of International Application PCT/FI2012/051067, filed Nov. 1, 2012, which international application was published on Aug. 8, 2013, as International Publication No. WO2013/113977. The international Application claims priority to U.S. Provisional Patent Application No. 61/592,842, filed Jan. 31, 2012, the contents of which are incorporated herein by reference in their entireties.

FIELD

The present invention relates to the manufacture of hydrocarbons useful as base oil components from bio-oils and fats. More specifically, the present invention relates to production of linear base oil range hydrocarbons by increasing the hydrocarbon chain length of a feedstock originating from renewable raw materials via a catalytic reaction.

BACKGROUND

The use of recycled oils and renewable raw materials in the production of transportation fuels and lubricants is an object of interest. The use of renewable raw materials of biological origin instead of non-renewable fossil raw materials for production of hydrocarbon components is desirable. The fossil raw materials are exhaustible and they have harmful effects on atmosphere and environment.

Bio-oils have previously been transesterified to form biodiesel (fatty acid methyl esters; FAME) and biolubricant components (lube esters). The use of lube esters is limited to a few special applications such as oils for refrigerator compressor lubricants, bio-hydraulic oils and metal working oils. In regular automotive and industrial lubricants, esters are used mainly in additive scale, because of technical problems associated with the lube esters. Lube esters are polar compounds and suffer greater seal-swelling tendency than pure hydrocarbons. In addition, lube ester oils are hydrolyzed more easily to acids, which in turn cause corrosion on lubricating systems. Lubrication oils consisting of pure hydrocarbon structures do not suffer from these problems. It is therefore desirable to find ways of producing hydrocarbon lube oil components from renewable sources.

High molecular weight components can be produced from free fatty acids in a method where two free fatty acids react with each other forming a ketone. The carbon number of the formed ketone back-bone is the sum of the carbon atoms in the two fatty acids minus one carbon, due to the release of one molecule of $CO_2$ during ketonization. The catalysts used in these reactions are metals or oxides of alkaline earth metals. Metal oxide catalysts do no deoxygenate the formed ketones.

Metal oxide ketonization catalysts suffer from several drawbacks. The catalysts cannot tolerate double bonds or triglycerides during the ketonization, of which both are typically present in bio-oils. Therefore, double bonds must first be saturated and triglycerides are removed prior to the ketonization unit. This is typically performed by distilling the free fatty acids and employing a pre-hydrogenation unit before the actual ketonization unit. The ketonization units therefore can require a very cumbersome pre-treatment of the triglyceridic bio-oils.

In addition, ketonization reaction of fatty acids is typically done using gas phase introduction of free fatty acids. Due to the low vapor pressure of fatty acids, vaporisation of fatty acids needs much energy and carrier gas, which can require a large unit.

Formation of hydrocarbon lube components by ketonization of free fatty acids, using a metal oxide catalyst in gas phase, is demonstrated in WO2007068795. The formed ketones were further hydrodeoxygenated and isomerized and paraffinic lube oil components were produced. EP 591297 describes a method for producing a ketone from fatty acids by pyrolysis reaction using a magnesium oxide catalyst. EP 0457665 discloses a method for producing ketones from triglycerides, fatty acids, fatty acid esters, fatty acid salts, and fatty acid anhydrides using a bauxite catalyst containing iron oxide. All these methods suffer from the above described disadvantages.

High molecular weight compounds have also been reported in publication EP1741768 as unwanted side-reaction products in hydrodeoxygenation reactions of biological oils and fats. The side-reactions, such as oligomerization and even polymerizations, are due to uncontrolled reactions involving the double bonds of the biological oils (unsaturated fatty acids). These high molecular weight compounds are a nuisance in HVO (hydrogenated vegetable oil) production in form of lowered middle distillate yield as well as coking and de-activation of the catalyst.

Publication US 2011107656 describes a method for processing triglyceride-containing, biologically-derived oils to provide for base oils and diesel fuels, wherein partial oligomerization of unsaturated fatty acids contained therein yields a mixture from which the base oils and diesel fuels is extracted. Dimerization, trimerization or oligomerization of unsaturated fatty acids forms, after hydrodeoxygenation, highly branched and cyclic hydrocarbon components and even aromatic compounds are formed. Viscosity index of these mixtures is greater than 120.

Therefore, there is an obvious need for a method to produce nonpolar saturated base oil components complying with the high quality requirements from renewable sources avoiding the above disclosed problems.

SUMMARY OF THE INVENTION

The object of the present invention is to provide a method for increasing the hydrocarbon chain length without the need to use a regular ketonisation catalyst.

A further object of the present invention is to provide a method for production of components suitable for use in base oil production of especially high quality.

It was surprisingly found that hydrotreatment catalysts can be applied and are able to carry out the production of linear base oil range ketones without operational problems. The production of base oil components can be performed on a feedstock containing high concentration of free fatty acids.

The formed ketones are preferably further hydrodeoxygenated in a final hydrodeoxygenation step to n-paraffins. The base oil range paraffins formed according to this invention by a ketonization reaction of fatty acids or fatty acid esters form a $C(2n-1)$-paraffin from two $C(n)$-fatty acids. Biological oils and fats predominantly contain C16 and C18 fatty acids from which C31, C33 and C35 paraffins are obtained through ketonisation. The formed n-paraffins are preferably isomerized to produce high quality base oil components.

In the first aspect of the present invention a method for increasing the hydrocarbon chain length of fatty acids is disclosed as depicted by claim 1.

In the second aspect a method for simultaneous production of base oil components and fuel components is disclosed as depicted by claim 12.

The advantages of the method of the present invention are that the hydrotreatment catalyst is able to function efficiently and withstand conditions typically considered challenging for a ketonisation catalyst. The use of the hydrotreatment catalyst enables the presence of double bond containing compo-nents or triglyceridic components in the feedstock. Catalytic deactivation can be suppressed. The feedstock can comprise free fatty acids, in particular, in a high concentration. Moreover, the feedstock can be introduced to the ketonisation reaction zone in liquid phase, thereby avoiding cumbersome vaporization of the feedstock.

DETAILED DESCRIPTION

Definitions

Ketonization means the formation of a ketone through a chemical reaction. The ketone can be formed from an oxo-compound such as an alcohol, ester, aldehyde, carboxylic acid or other suitable oxygen containing starting material. Here "ketonization of fatty acids" means the reaction of two fatty acids producing a linear ketone. Typically the fatty acids present in bio-oils have a carbon number of at least 10 and the formed ketone thus has a carbon number in base oil range.

Here "lubricant" means oil which consists of base oil components and additives.

Here "base oil" means oil molecules, which can be used as lubricant components. Base oils carbon number range is from about ≥C24-C43.

Viscosity index is a measure of base oil, which tells how much viscosity of base oil changes with temperature. The higher value means better base oil, which can maintain its viscosity better at broader temperature range. Base oil has low enough viscosity running at cold temperature and is still viscous enough at high temperature.

Here "hydrotreatment" is understood as a catalytic process, which removes oxygen from organic oxygen compounds as water (hydrodeoxygenation, HDO), sulfur from organic sulfur compounds as dihydrogen sulfide (H2S) (hydrodesulfurisation, HDS), nitrogen from organic nitrogen compounds as ammonia (NH3) (hydrodenitrogenation, HDN) and halogens, for example chlorine from organic chloride compounds as hydrochloric acid (HCl) (dehydrochlorination, HDCl) typically under the influence of sulfided NiMo or sulfided CoMo catalysts.

Here "deoxygenation" is understood to mean the removal of oxygen from organic molecules, such as fatty acid derivatives, alcohols, ketones, aldehydes or ethers by any means previously described.

Here "hydrodeoxygenation (HDO) of triglycerides or other fatty acid derivatives" is understood to mean the removal of oxygen as water by the means of molecular hydrogen under the influence of catalyst.

Here "decarboxylation/decarbonylation" of triglycerides or other fatty acid derivatives is understood to mean removal of oxygen as $CO_2$ (decarboxylation) or as CO (decarbonylation) with or without the influence of molecular hydrogen. Decarboxylation and/or decarbonylation reactions are together referred to as decarb-reactions.

Here "hydrocracking" is understood as catalytic decomposition of organic hydrocarbon materials using molecular hydrogen at high pressures.

Here "hydrogenation" means saturation of carbon-carbon double bonds by means of molecular hydrogen under the influence of a catalyst.

Here "isoparaffins" means alkanes having one or more side chains, typically mono-, di-, tri- or tetramethylalkanes.

Here purification of feedstock is understood as removal of impurities such as metals and phosphorus.

Feedstock

Typical basic structural unit of plant and fish oils and animal fats is a triglyceride. Triglyceride is an ester of glycerol with three fatty acid molecules having the structure below:

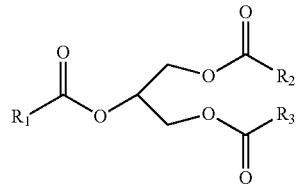

wherein $R_1$, $R_2$ and $R_3$ represent C4-C26 hydrocarbon chains i.e. chains with a carbon number from 4 to 26. Length of the hydrocarbon chain is typically 18 carbons (C18). C18 fatty acids are typically bonded to the middle hydroxyl group of glycerol. Typical carbon numbers of the fatty acids linked to the two other hydroxyl groups are even, being generally between carbon numbers C14 and C22.

The feedstock of the present invention comprises fatty acids and/or fatty acid esters originating from renewable sources such as plant oils, fish oils and animal fats. Preferably, the fatty acid esters are triglycerides such as those of formula 1. Triglycerides in the feedstock are preferably partially hydrodeoxygenated and partially decomposed to components which are able to further undergo a ketonisation reaction and a subsequent hydrodeoxygenation step. Therefore, ketonisation can be achieved even though the feedstock contains only fatty acids esters, such as triglycerides.

Starting materials originating from biological sources contain high amounts of oxygen. In addition, starting materials of biological origin often contain nitrogen, sulfur, phosphorus and metals. The impurities are often catalyst poisons and inhibitors of noble metal catalysts. They cause decreased service life of the catalyst, and make frequent regeneration of the catalysts necessary. Noble metal catalysts are used in isomerization processes. They are very expensive and highly sensitive to catalyst poisons. Therefore, it is often necessary to purify the feedstock for removal of unwanted contaminants, such as metals and phosphorous compounds. Purification method includes, but is not limited to, degumming and bleaching.

In one embodiment the fatty acids and/or fatty acid ester to be used in the present invention are the result of some processing step, such as thermal pyrolysis treatment. In another embodiment the fatty acids originating from transesterification and hydrolysis processes are used as feedstock in the present invention.

Production of Components Suitable for Base Oil Production by a Ketonisation Reaction Disclosed is a method for production of components suitable for use in base oil production by ketonisation of fatty acids and/or fatty acid esters over a hydrotreatment catalyst. The hydrotreatment catalyst can hydrogenate double bonds and remove oxygen from oxygenate components. Therefore, a separate double bond saturation unit is not needed for these purposes. The method according to the present invention can also operate with triglycerides and unexpected high concentrations of free fatty acids.

In a first aspect, the present invention provides a method for increasing hydrocarbon chain length. This method comprises the steps of providing a feedstock comprising fatty acids and/or fatty acid esters with a hydrocarbon chain length below C23 and introducing said feedstock into a reaction zone in which ketonisation reaction is conducted involving said fatty acids and/or fatty acid esters. The ketonisation reaction is performed in the presence of a hydrotreatment catalyst under hydrogen pressure. In the ketonisation reaction the hydrocarbon chain length is increased and ketones with hydrocarbon chain length from C24 to C43 are formed and obtained from said reaction zone.

During the ketonisation reaction, fatty acids of the feedstock are to some extent deoxygenated, denitrogenated and desulphurisated. The starting material, comprising fatty acids and/or fatty acid ester, is preferably partly transformed also into middle distillate range C10-C20 n-paraffins simultaneously with the formation of base oil range C24-C43 molecules. During the hydrotreatment of fatty acids $H_2O$, $CO_2$, CO, $H_2S$ and $NH_3$ gases are released and removed from liquid oil products. If triglycerides are fed also propane is formed.

Decomposition of triglycerides and fatty acid derivatives forms compounds, such as free fatty acids, which can subsequently undergo ketonisation reactions. The mild hydrotreatment conditions under the ketonisation reaction facilitate also hydrogenation of the double bonds. Saturation of double bonds is kinetically very fast and typically occurs before hydrodeoxygenation. Saturation of double bonds therefore minimizes uncontrolled oligomerisation reactions.

In one embodiment the ketonisation and hydrotreatment are performed in the same reaction zone. In another embodiment the ketonization reaction is followed by a further final hydrodeoxygenation step to form linear hydrocarbons. In another embodiment this final hydrodeoxygenation step is performed in a separate reaction zone under different hydrotreatment conditions compared to the ketonisation reaction subsequent to ketonisation.

During the ketonisation reaction, the pressure (overpressure) in the reaction zone is preferably less than 2 MPa (overpressure), more preferably less than 1.5 MPa, most preferably less than 1 MPa, such as below 0.5 MPa. Low hydrogen pressure enables saturation of the double bonds in fatty acids and drives the reaction towards formation of ketones, instead of oligomerisation. Thereby, catalyst lifetime is extended and less deactivation of the catalyst is observed. Coking of the catalyst bed is also diminished with the low hydrogen pressure. However, the mild hydrotreatment conditions still enable some hydrotreatment of the fatty acid material to middle distillate range n-paraffins as well as hydrotreatment of the formed ketones.

The temperature of the reaction zone is preferably from 200 to 450° C., but more preferable it is from 350 to 450° C., most preferably from 350 and 400° C.

The sulfur content in the feed may be varied from 0 w-ppm to 2000 w-ppm, calculated as elemental sulfur, preferably from 0 to 1000 w-ppm and most preferably from 0 to 500 w-ppm.

The feed flow rate WHSV is preferably from 0.1 to 10 1/h, more preferably from 0.3 to 5 1/h, most preferably from 0.3 to 3 1/h.

The ketonisation of fatty acids under hydrogen pressure is carried out contacting the feedstock with a hydrotreatment catalyst. The hydrotreatment catalyst is preferable a metal catalyst selected from the group consisting of Fe, Pd, Pt, Ni, Mo, Co, Ru, Rh, W and any combination thereof. More preferable, the metals are NiMo or CoMo, optionally with additional Mn, Fe, Pd, Pt metals. Most preferable, the catalyst is NiMo. The hydrotreatment catalyst is preferable supported, wherein the supports are laterite, bauxite, titanium dioxide, active carbon, silica and/or alumina, most preferably active carbon, silica and alumina.

Most preferable the hydrotreatment catalyst is a NiMo catalyst on an alumina support.

In a preferred embodiment the hydrotreatment catalyst is a sulfided hydrotreatment catalyst.

Final Hydrodeoxygenation Step

A final hydrodeoxygenation (HDO) step is preferably performed under a hydrogen gas pressure ranging from 0.1 to 20 MPa, preferably from 1 and 15 MPa, more preferably from 2 to 10 MPa. The temperature ranges from 100 to 500° C., preferably from 150 to 400° C., more preferably from 200 to 350° C. The flow rate, WHSV, is preferably varied from 0.1 to 10 1/h, more preferably from WHSV 1 to 5 1/h, and most preferably from WHSV 1 to 3 1/h. In this final hydrogenation step, catalysts containing a hydrogenation metal, on a support are used. Preferably, the HDO catalyst is a supported Pd, Pt, Ni, NiMo or CoMo catalyst, the support being activated carbon, alumina and/or silica.

The deoxygenation of plant oils/fats and animal fats with hydrogen (HDO) uses rather much hydrogen and at the same time releases significant amount of heat. Heat is produced from deoxygenation reactions and from double bond hydrogenation. Different feedstocks produce significantly different amount of reaction heat. The variations of reaction heat produced is mainly dependent of double bond hydrogenation therefore the feed sources like palm oil or animal fat, which has more saturated fatty acid derivatives, produce less heat. The average amount of double bonds per triglyceride molecule can vary from about 1.5 to over 5 depending on the source of bio oil or fat.

In order to control the increase of temperature over catalyst beds, fresh feedstock is typically divided between several catalyst beds and hydrotreated product is recycled through reactor beds in series.

Due to the bimolecular reaction of ketonisation, it is preferred in the present invention to use as concentrated fatty acid feed as possible. However, some product recycle dilution can be used, if needed. According to the present invention (product recycle)/(fresh feed)-ratio is preferably from 0 to 5, more preferably from 0 to 1. By the term "product" is meant any internal flow from the process that is suitable for being directed back to the process as recycle.

In a preferred embodiment the feedstock further comprises a diluent containing product recycle.

Another preferable way to handle reaction heat in the present invention is to use reaction conditions, which only partly deoxygenate triglycerides or fatty acids or fatty acid derivatives. This approach is also preferred for ketonisation of fatty acids because the efficient deoxygenation also destroys carboxylic groups in fatty acids and therefore the starting material for the ketonisation reaction. The ketonisation can be done using the hydrogen addition lower than the theoretical chemical consumption of hydrogen needed for complete deoxygenation, especially if a separate final hydrodeoxygenation step is applied. The preferred ratio of hydrogen to feedstock is from 100 to 600 Nl/l, more preferably from 100 to 300 Nl/l, most preferably from 130 to 250 Nl/l, such as from 150 to 230 Nl/l.

In one embodiment ketonisation of fatty acids is performed in the first catalyst bed of multi catalyst beds in series. The catalyst beds may be located in the same pressurized reactor or several pressurized reactors. In another embodiment ketonization of fatty acids is performed in the first reaction zone and the final hydrodeoxygenation and/or hydrogenation is completed in the next reaction zone. Using this procedure the co-production of base oil components and bio fuel components can be done efficiently. After the catalyst bed the product stream is optionally cooled using a heat exchanger or colder fresh feed. During the final hydrodeoxygenation step excess hydrogen is fed into the reaction zone according to the theoretical chemical hydrogen consumption.

Isomerization of n-Paraffins

Advantageously, it is possible to use high concentration of free fatty acids, low dilution and same or increased reaction temperature during the ketonisation reaction of the present invention. Obtained n-paraffins are converted into diesel and base oil range branched alkanes using isomerization, with high base oil component yield. Isomerization of base oil components and diesel compounds can be done at same reactor or separated reactors. The hydrocarbon oil formed via this process is a high quality bio base oil and renewable diesel component and/or optionally bio-jet and/or biogasoline. The formation of base oil components is preferably performed in low pressure, high temperature and low amount of hydrogen. The pressure and the temperature of the ketonisation reaction zone are preferably selected to maintain at least part of said feedstock in liquid phase. Thus, there is no need of prior vaporisation of fatty acids resulting in no high flow carrier gas circulation. This enables use of smaller operational units.

The n-paraffins formed by hydrodeoxygenation of ketones can be hydroisomerised and produce short branch (C1-C3) iso-paraffins.

Isomerization of C24-C43-paraffins to isoparaffins is preferably performed in order to improve cold flow properties of compounds produced. Hydroisomerization of diesel paraffins is known and is typically performed performed using noble metal bifunctional catalysts, preferably Pt-SAPO or ZSM-catalysts at reaction temperature 300-400° C., pressure 20-40 bar and space velocity WHSV from 0.5 to 2 $h^{-1}$ with hydrogen.

Isomerization of n-paraffins does not as such need hydrogen, but it is important that olefins formed from cracking (side reaction) are quickly hydrogenated. Without the fast olefin saturation, coking of catalyst is observed.

Due to the longer chains of base oil range n-paraffins (C24-C43) compared to diesel paraffins (carbon number typically below 24), isomerization is more challenging. In order to get good cold flow properties of n-paraffins (C24-C43) more severe isomerization is needed. At the same time the probability to cracking is higher when n-paraffins are longer. On the other hand, when C24-C43 molecules crack, excellent diesel and jet molecules are produced, but when diesel range molecules crack, rather low grade gasoline molecules and gas components are produced.

In a second aspect of the present invention a method for simultaneous production of base oil components and fuel components is provided as depicted by claim 12. The method comprises (i) introducing a feedstock comprising fatty acids and/or fatty acid esters into a reaction zone in which ketonisation and hydrotreatment of said fatty acids is conducted in the presence of a hydrotreatment catalyst and under hydrogen pressure, wherein the formed ketones are subsequently hydrodeoxygenated to form linear hydrocarbons, wherein the ketonisation and hydrodeoxygenation are optionally performed in the same reaction zone;

(ii) introducing the material resulting from (i) into an isomerization unit wherein a mixture of branched hydrocarbons is formed, and (iii) separating from said mixture hydrocarbons suitable for use as base oil components having a carbon number range from C24-C43 from hydrocarbons suitable for use as fuel components having a carbon number range from C5 to C20.

Advantageously, due to the integrated production process, less unit operations and less reaction steps are required rendering the production more efficient than earlier.

The present invention is further illustrated by the following non-limiting examples.

EXAMPLES

Example 1

A composition, consisting of saturated stearic fatty acid (derived from vegetable oil), diluted with paraffinic co-feed in ratio of 1:1, was subjected to hydrotreatment. Treatment

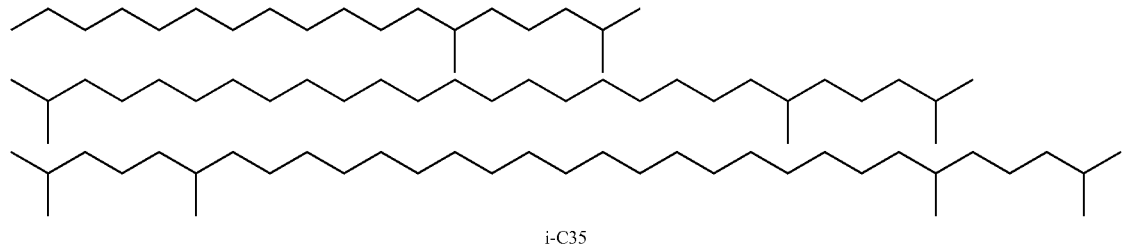

i-C35 was carried out in three different conditions (tests 1-3) in presence of a sulphidized NiMo catalyst on alumina support. WHSV and hydrogen to hydrocarbon ratio is calculated from the amount of saturated fatty acid feed in vessel. Process conditions and hydrocarbon distribution yields are presented in table 1.

TABLE 1

Process conditions in hydro treatment and product distribution

| Test | Catalyst | Reactor Conditions | | | | | |
|---|---|---|---|---|---|---|---|
| | | Temp. °C. | Pressure MPa | H2/HC Nl/l | WHSV 1/h | ≥C24 % | C11-C23 % |
| 1 | NiMo + S | 365 | 0.40 | 150 | 0.50 | 1.1 | 92.7 |
| 2 | NiMo + S | 365 | 0.20 | 150 | 0.50 | 5.1 | 89.8 |
| 3 | NiMo + S | 365 | 0.25 | 100 | 0.50 | 13.6 | 81.4 |

The obtained products were analyzed with gas chromatography. Ketones are identified in the gas chromatograms, which indicate that linear high molecular paraffins are formed through ketonization reactions.

Example 2

A mixture of saturated stearic fatty acid (30 wt-%) (derived from vegetable oil), and rape seed oil (70 wt-%) was subjected to hydrotreatment. Treatment was carried out in presence of sulphidized NiMo catalyst (on alumina carrier) at conditions shown in table 2. Hydrocarbon distribution of the products formed is shown in table 2.

TABLE 2

Process conditions in hydro treatment and product distribution

| Test | Catalyst | Reactor Conditions | | | | | |
|---|---|---|---|---|---|---|---|
| | | Temp. °C. | Pressure MPa | H2/HC Nl/l | WHSV 1/h | ≥C24 % | C11-C23 % |
| 1 | NiMo + S | 365 | 0.7 | 200 | 0.5 | 29.5 | 57.5 |

The obtained products were analyzed with gas chromatography. Ketones are identified in the gas chromatograms, which indicate that linear high molecular paraffins are formed through ketonization reactions.

The above examples show that it is possible to co-produce diesel range hydrocarbons components together with base oil components in the same reactor conditions using only a hydrotreatment catalyst.

The invention claimed is:

1. A method for increasing hydrocarbon chain length, comprising the steps of:
    (i) introducing a feedstock comprising fatty acids and/or fatty acid esters having hydrocarbon chain lengths below C23 into a ketonization reaction zone,
    (ii) subjecting said feedstock to ketonization and hydrotreatment reactions in the presence of a hydrotreatment catalyst under hydrogen pressure to produce an effluent comprising ketones, and
    (iii) obtaining ketones having hydrocarbon chain lengths of from C24 to C43 from said effluent.

2. The method according to claim 1, wherein the obtained ketones are further hydrodeoxygenated in a final hydrodeoxygenation step to form linear hydrocarbons.

3. The method according to claim 2, wherein the ketonization and final hydrodeoxygenation step are performed in the ketonization reaction zone.

4. The method according to claim 2, wherein the final hydrodeoxygenation step is performed in a separate reaction zone from the ketonization reaction zone subsequent to the ketonization reaction.

5. The method according to claim 1, wherein the pressure in the ketonization c on zone is less than 2 MPa.

6. The method according to claim 1, wherein the temperature in the ketonization reaction zone is from 350 to 450° C.

7. The method according to claim 1, wherein the ratio of hydrogen to feedstock is from 100 to 600 Nl/l in the ketonization reaction zone.

8. The method according to claim 1, wherein said hydrotreatment catalyst is a metal catalyst wherein the metal is selected from the group consisting of Fe, Pd, Pt, Ni, Mo, Co, Ru, Rh, W and any combination thereof.

9. The method according to claim 8, wherein said hydrotreatment catalyst is NiMo or CoMo.

10. The method according to claim 1, wherein said hydrotreatment catalyst is a sulfided hydrotreatment catalyst.

11. The method according to claim 1, wherein said hydrotreatment catalyst is on a support.

12. A method for simultaneous production of base oil components and fuel components, the method comprising:
    (i) introducing a feedstock comprising fatty acids and/or fatty acid esters into a reaction zone,
    (ii) subjecting said feedstock to ketonization and hydrotreatment reactions in the presence of a hydrotreatment catalyst under hydrogen pressure to produce ketones,
    (iii) hydrodeoxygenating said ketones to form linear hydrocarbons, wherein the ketonization reaction and the hydrodeoxygenating are performed in the same reaction zone or separate reaction zones,
    (iv) isomerizing the linear hydrocarbons in an isomerization unit to produce a mixture of branched hydrocarbons, and
    (v) separating from said mixture of branched hydrocarbons a base oil fraction comprising hydrocarbons having carbon numbers in a range of C24-C43 and a fuel components fraction having carbon numbers in a range of C5 to C20.

13. The method of claim 11, wherein the hydrotreatment catalyst is on a support of activated carbon, alumina, or silica.

* * * * *